(12) United States Patent
Oroskar et al.

(10) Patent No.: US 8,658,845 B2
(45) Date of Patent: Feb. 25, 2014

(54) PROCESS AND ADSORBENT FOR SEPARATING ETHANOL AND ASSOCIATED OXYGENATES FROM A BIOFERMENTATION SYSTEM

(75) Inventors: Anil R. Oroskar, Oak Brook, IL (US); Deepak Sharma, Naperville, IL (US); David W. House, Arlington Heights, IL (US); Alice M. Havill, Parnell (NZ)

(73) Assignee: Orochem Technologies, Inc., Naperville, IL (US)

( * ) Notice: Subject to any disclaimer, the term of this patent is extended or adjusted under 35 U.S.C. 154(b) by 153 days.

(21) Appl. No.: 13/478,160

(22) Filed: May 23, 2012

(65) Prior Publication Data

US 2013/0317260 A1    Nov. 28, 2013

(51) Int. Cl.
*C07C 29/76* (2006.01)

(52) U.S. Cl.
USPC .......... 568/913; 568/917; 435/161; 435/132; 435/140

(58) Field of Classification Search
USPC ............. 568/913, 917; 435/161, 132, 140
See application file for complete search history.

(56) References Cited

U.S. PATENT DOCUMENTS

| | | | |
|---|---|---|---|
| 2,985,589 | A | 5/1961 | Broughton |
| 4,321,328 | A | 3/1982 | Hoge |
| 4,333,740 | A | 6/1982 | Priegnitz |
| 5,156,736 | A | 10/1992 | Schoenrock |
| 5,755,967 | A | 5/1998 | Meagher |
| 6,476,239 | B1 | 11/2002 | Arumugam et al. |
| 6,872,314 | B2 | 3/2005 | Boyd |
| 6,896,811 | B2 | 5/2005 | Heikkila |
| 7,166,460 | B2 | 1/2007 | Wilkins |
| 7,229,558 | B2 | 6/2007 | Heikkila et al. |
| 7,399,898 | B2 | 7/2008 | Lee |
| 7,507,273 | B1 | 3/2009 | Massie |
| 8,119,378 | B2 | 2/2012 | Simpson |
| 2006/0251762 | A1 | 11/2006 | Jansen |
| 2010/0099155 | A1 | 4/2010 | Frank |
| 2010/0204526 | A1 | 8/2010 | Kouba et al. |
| 2010/0323417 | A1 | 12/2010 | Simpson |
| 2011/0160483 | A1 | 6/2011 | Rezkallah |
| 2012/0330043 | A1 | 12/2012 | Kelliher et al. |

FOREIGN PATENT DOCUMENTS

WO    2008046635 A1    4/2008

OTHER PUBLICATIONS

Ken-Jer Wu, Saratale, Gd., Lo, Y., Chen, W., Tseng, Z., Chang, M. Tsai, B., Su, A., Chang, J., "Simultaneous Production OD 2,3-Butanediol, Ethanol and Hydrogen With *Klebsiella* sp. Strain Isolated From Sewage Sludge", Bioresource Technology, 2008, vol. 99, pp. 7966-7970, Elsevier.

A.N. Anozie, Okuhon, EE, Osoulale, FN, Adewole, JK, Dehydration of Ethanol-Water Mixture Using Activated Carbons From Sawdust and Palm Kernel Shells, Separation Science and Technology, vol. 45, pp. 1482-1489, Published Online Jun. 15, 2010, Taylor & Francis, England.

ISR and WO related to corresponding application PCT/US2013/041850, mailed Sep. 23, 2013, by KIPO.

*Primary Examiner* — Elvis O Price

(74) *Attorney, Agent, or Firm* — Richard P. Silverman & Assoc., LLC

(57) ABSTRACT

Disclosed is a process and an adsorbent for the separation of ethanol associated oxygenates from a dilute mixture of ethanol and associated oxygenates in water in the presence of organic compounds derived from a biofermentation process. After pretreatment, the separation is carried out in a simulated moving bed adsorption system employing an stationary phase adsorbent comprising fluorinated carbon or modified C18 silica gel selective for the adsorption of ethanol and associated oxygenates, such as 2,3-butanediol, with a mobile phase desorbent selected from the group consisting of methanol, ethanol, propanol, and methyl tertiary butyl ether. The process is useful for removing water from dilute aqueous mixtures of organic compounds comprising ethanol in dilute concentration in water and produced by fermentation, biomass extraction, biocatalytic and enzymatic processes which are not economically recoverable by conventional distillation methods.

35 Claims, 7 Drawing Sheets

PROCESS AND ADSORBENT FOR SEPARATING ETHANOL AND ASSOCIATED OXYGENATES FROM A BIOFERMENTATION SYSTEM

FIELD OF THE INVENTION

This invention is concerned generally with the recovery and purification of ethanol and associated oxygenates such as butanediol from biofermentation systems. The method provides for the separation of ethanol and associated oxygenates from dilute aqueous mixtures in the presence of oxygenated organic compounds. More particularly, the invention relates to an effective adsorbent for use in a simulated moving bed adsorption process for the selective separation of ethanol and 2,3 butanediol from a dilute aqueous solution of ethanol and 2,3 butanediol in the presence of biofermentation system products.

BACKGROUND

The separation of organic compounds from water has been an ongoing challenge for the chemical industry. Typically, techniques such as distillation, decantation, extraction, evaporation, and chromatography have been employed. These methods, however, often are energy intensive, expensive to operate, and may not be practical or economical for the recovery and purification of materials from dilute aqueous solutions. For example, chemical products such as glucose, which is isolated from biomass, and fermentation products such as lactic acid, phenylalanine, citric acid, L-amino acids, succinic acid, and ascorbic acid, typically must be separated, recovered, and purified from dilute aqueous solutions or fermentation broths. The recovery costs for such fermentation processes are often the major factor which determines their commercial success. The presence of water in chemical products also often complicates purification methods such as crystallization, waste disposal methods, such as incineration, and the recovery and recycling of solvents.

Over forty years ago, a new process was developed specifically for large scale industrial purifications. U.S. Pat. No. 2,985,589 disclosed a chromatography system involving a separation tower divided into a number of individual separation beds. These beds are connected in series, and the outlet at the bottom most bed is connected to a pump that returned flow in a continuous loop to the upper most bed. The inlet apparatus for each bed has a port connected to a downward flowing conduit. The conduits terminate in fittings attached to a rotary valve designed to control both ingress and egress of liquids into or from the inlets to each individual bed. The system is called Simulated Moving Bed (SMB) chromatography because the beds appear to be moving in a direction countercurrent to the direction of flow. There are hundreds of adsorbents which have been used for simulated moving bed systems, some of which include resins, zeolites, alumina, and silica.

Simulated Moving Bed (SMB) technology represents a variation on the principles of high performance liquid chromatography. SMB can be used to separate particles and/or chemical compounds that would be difficult or impossible to separate by any other means. Furthermore, SMB technology represents a continuous process which provides a significant economic and efficiency advantages in manufacturing operations compared to batch typical batch separation methods including crystallization and stepwise chromatographic separations.

The continuous nature of SMB operation is characterized by very brief flow stoppages during the port switchovers in successive process steps. However, since all input and output conduits briefly stop at the same time, there are no significant pressure drops or surges in the system. Indexing of mechanical rotors is designed to effect rapid switchovers, even on very large industrial machines. Further, strategy in the design of process configuration is largely dictated by the affinity and release characteristics of bound species to the solid substrate, exclusion properties of unbound species, the bed volume required to obtain separation of by-product, and other factors.

There are more than 200 issued patents on modifications of SMB technology that disclose improvements in separation efficiency generally, or in particular applications, enhanced purity and yield in the final products, or reduction in required volume desorbent. For example, in one variation disclosed in U.S. Pat. No. 5,156,736, separations are performed in a single bed preserving the principles of SMB by interposing at various levels in the bed a series of crossectionally functional collection and distribution means for adding feedstock and recycled process liquid, collecting raffinate, distributing eluent, and recovering extract product. Equilibrium is established in the system by very precise flow and pressure control.

U.S. Pat. No. 4,333,740 discloses an absorptive process for separating water from a feed mixture comprising ethanol and water, which comprises contacting the feed mixture with an adsorbent comprising corn meal, selectively adsorbing substantially all of the water to be separated to the substantial exclusion of the ethanol, and thereafter recovering high purity ethanol. The process employs a countercurrent moving bed or simulated moving bed countercurrent flow system.

In U.S. Pat. No. 5,755,967 discloses the use of a new composite membrane and a method for recovery of acetone and butanol using pervaporation. In the technique molecules are selectively adsorbed by a membrane and are caused to diffuse across the membrane through a driving force such as vacuum.

U.S. Pat. No. 7,166,460 discloses a bioprocess engineering solution for a product removal process for use in biofermentation. The invention discloses a process for withdrawing an aliquot of broth from a biofermentation vessel during at least a portion of the biofermentation, removing biocatalyst and water, chromatographically separating biofermentation products from the withdrawn broth using water as an eluent, and returning the remaining components of the broth back to the biofermentation vessel. The continuous chromatic separation process is disclosed to be counter-current chromatography or simulated counter-current chromatography, including simulated moving bed chromatography. However, the reference states that process chromatography methods are unable to selectively separate biofermentation products and recycle the other media components to the biofermentor. This occurs because a portion of the eluent required to drive chromatographic separation would accumulate in the biofermentor, reducing its capacity.

US Publication No. 2010/0099155 discloses apparatuses and processes for the removal and production of fermentation prepared one or more volatile organic compounds. The apparatuses comprise a fermentor unit, a vacuum side stripper unit, and optionally one or more pressure swing adsorption unit, a dual-function column, a dividing wall distillation column, and a means for inducing phase separation of a mixture of volatile compounds and water.

The known methods for dewatering organic compounds are limited primarily to organic acids and typically utilize a strong charge-charge interaction between the acid and adsorbent, such as ion-exclusion, as the primary separation mechanism. Because such charge-charge interactions are weak or non-existent for neutral organic compounds, these methods are not, in general, applicable for dewatering organic compounds without carboxyl substituents.

The object of the present invention is to provide methods for concentrating ethanol streams derived from biofermentation processes.

It is a further object of the invention to remove dilute ethanol and 2,3-butanediol from a fermentation broth and to concentrate the dilute ethanol and 2,3-butanediol.

It is a still further object of the invention to provide methods for concentrating and recovering ethanol from fermentation products

SUMMARY OF THE INVENTION

The invention relates to process and to adsorbents for the separation of ethanol from a dilute mixture of ethanol in water in the presence of organic compounds derived from a biofermentation process, wherein in part, the separation is carried out in a simulated moving bed adsorption system. Conventionally, by distillation methods, the separation of ethanol from biomass effluent has an energy requirement of about 30000 BTU/gallon (about 2000 Kcal/L) of ethanol produced. This is in large part because of the high energy requirement for distillation of ethanol from water. The energy consumption of the present invention to achieve the same separation potentially reduces this energy requirement by about 75 percent. Furthermore, the SMB process enables the commercial recovery of other associated oxygenate components in the biomass effluent such as isopropyl alcohol (IPA), butanol (BuOH), n-butanol, t-butanol, hydroxymethyl-tetrahydrofuran or tetrahydro-2-furfuryl alcohol (THFA), propane diols, 1,2-propanediol, 1,3-propanediol, butanediols, 1,2-butanediol, 1,3-butanediol, 1,4-butanediol, 2,3-butanediol, pentane diols, 1,2-pentanediol, 1,5-pentanediol, 1,8-octanediol, etohexadiol, p-menthane-3,8-diol, 2-methyl-2,4-pentanediol, aldehydes, propanal, butanal, 2,5-furan-diacrboxyaldehyde, carboxylates, acetic acid, oxopropanoic acid, acrylic acid, levulinic acid, succinic acid, 2,5-furan-dicarboxylic acid, aspartic acid, glucaric acid, glutamic acid, itaconic acid, acetylacrylic acid, 4-O-Me-glucuronic acid, gluconic acid, and xylonic acid. The process is useful for removing water from aqueous mixtures of organic compounds produced by fermentation, biomass extraction, biocatalytic and enzymatic processes. It was surprisingly discovered that a particular combination of stationary phase adsorbents and desorbents in a simulated moving bed process could successfully be used to dewater dilute aqueous ethanol streams to provide a concentrated ethanol stream which could more efficiently be further processed to provide commercial ethanol streams.

In one embodiment, the invention is a continuous SMB process for the recovery of ethanol from a biomass effluent stream from a fermentor. The biomass effluent stream comprises water, ethanol, at least one associated oxygenate, acetic acid and suspended solids. The SMB process comprises a desorption zone, a rectification zone, an adsorption zone, and a regeneration zone as SMB zones. Each SMB zone has an upper portion and a bottom portion. The desorption zone, the rectification zone, the adsorption zone and the regeneration zone each comprises one or more serially-linked adsorbent beds. Each adsorbent bed contains a stationary phase adsorbent selective for the adsorption of ethanol and the at least one associated oxygenate.

In the denaturation zone the biomass effluent stream is denatured to provide a denatured biomass effluent stream and in the filtration zone the denatured biomass effluent stream is filtered through a filter having a filter size of less than or equal to 5 microns. The filtered and denatured biomass effluent stream is pH adjusted to a pH between about 5 and about 10 to provide a treated biomass effluent stream comprising water, at least one associated oxygenate, acetic acid and soluble biomass The SMB process comprises passing the biomass effluent stream to a pretreatment zone comprising a denaturation zone and a filtration zone. In the denaturation zone the biomass effluent stream is denatured to provide a denatured biomass effluent stream and in the filtration zone the denatured biomass effluent stream is filtered through a filter having a filter size of less than or equal to 5 microns. The filtered and denatured biomass effluent stream is pH adjusted to a pH between about 5 and about 10 to provide a treated biomass effluent stream comprising water, at least one associated oxygenate, acetic acid and soluble biomass and having a concentration of ethanol and the at least one associated oxygenate of less than about 15 wt-% in water. The treated biomass effluent stream is introduced to the upper portion of the adsorption zone and a raffinate stream comprising water and a minor portion of ethanol is withdrawn from the bottom portion of the adsorption zone. A desorbent stream in a desorbent flow direction is passed to the upper portion of the desorption zone and a desorbent effluent stream is withdrawn from the bottom of the desorption zone and a portion of the desorption zone effluent stream is recovered as an extract stream comprising ethanol, the at least one associated oxygenate, acetic acid and a minor portion of water. A remaining portion of the desorption effluent stream is passed to the upper portion of the rectification zone and a rectification zone effluent is withdrawn. The rectification zone effluent is combined with the treated biomass effluent stream prior to introducing the treated biomass effluent stream to the upper portion of the adsorption zone. A regeneration zone is isolated and a hot regeneration stream at a regeneration temperature is passed to the upper portion of the regeneration zone and a spent regeneration stream is withdrawn from the bottom portion of the regeneration zone. The spent regeneration stream is cooled to provide a cooled spent regeneration stream. The extract stream is passed to a recovery zone to provide an ethanol product stream and an associated oxygenate product stream. The adsorbent beds are indexed sequentially in a direction which is counter current to the desorbent flow direction according to the SMB cycle.

DETAILED DESCRIPTION OF THE INVENTION

Figure 1:
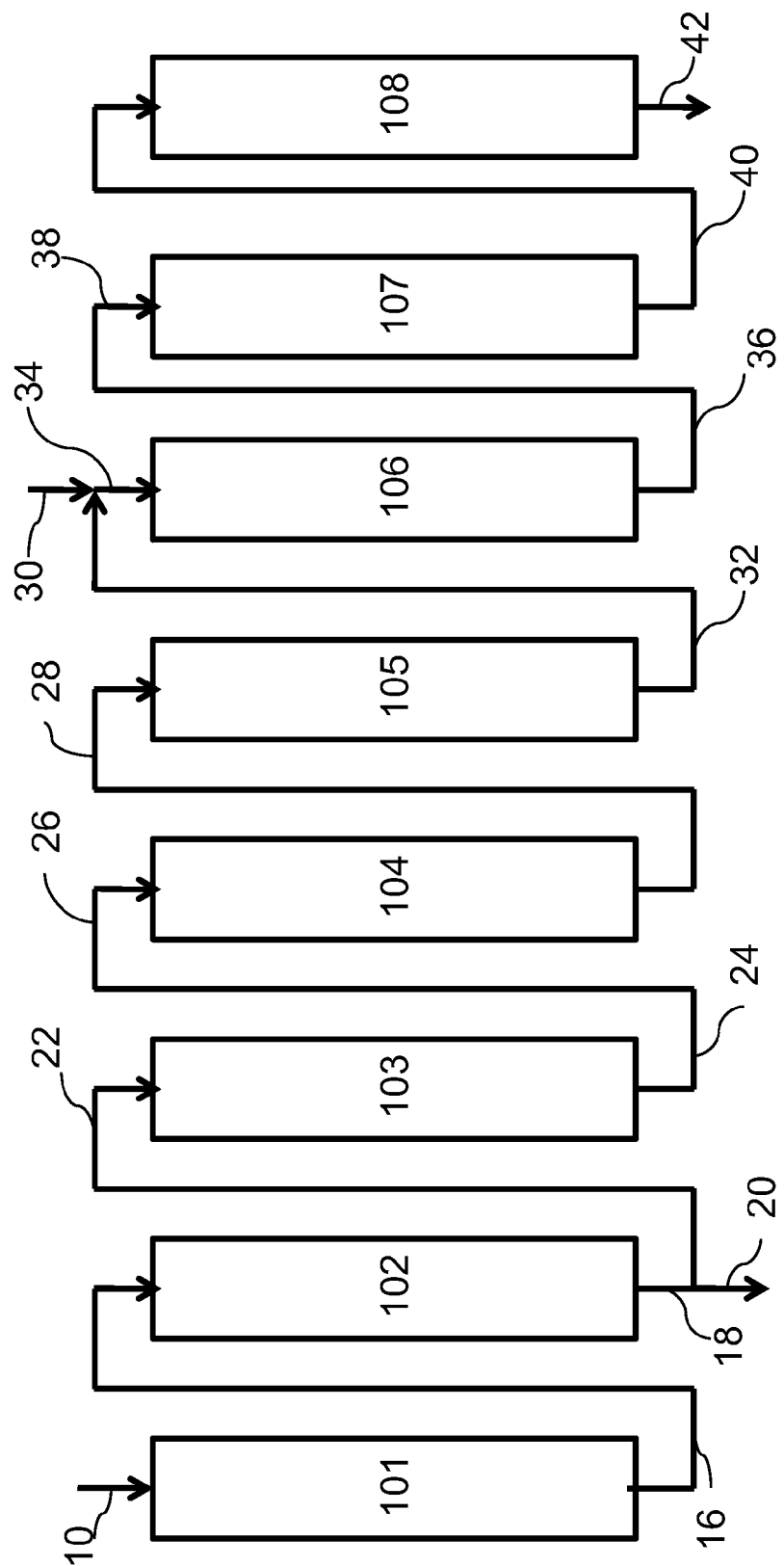
FIG. 1 is a schematic process flow diagram representing one embodiment of the present invention for a basic simulated moving bed adsorption process employing eight adsorption beds for the dewatering of ethanol.

The present invention relates to the surprising discovery that ethanol produced in a fermentation process can be separated from water in the presence of associated oxygenate components as discussed hereinabove, such as isopropanol, propanediols, and butanediols, in a simulated moving bed (SMB) process with a selective stationary phase adsorbent and a suitable desorbent.

SMB Feedstock Pretreatment

Biofermentation processes provide a fermentation product stream which comprises water, ethanol, non-condensable gases such as methane, nitrogen, carbon dioxide, and hydrogen, oxygenated organic compounds and soluble biomass materials. Oxygenated chemicals such as ethanol have been traditionally produced from sugar sources, such as corn, sugarcane, molasses, etc. Other associated oxygenates produced with ethanol by fermentation often include isopropanol, propanediols, butanediols, and acetic acid. For example, it is well known that 2,3-butanediol can be produced by fermentation techniques. Examples of some species of bacteria such as *Bacillus polymyxa* and *Klebsiella pneumoniae* have been disclosed to convert both glucose and xylose into mixtures of predominantly 2,3 butanediol and ethanol. Also, the production of 2,3-butanediol has been disclosed using arabinose as a feedstock. A summary of such methods entitled, "Bulk Chemicals from Biomass", by Jacco van Haveren, et al. was published online in Wiley InterScience. More recently, ethanol has been produced by the fermentation of gases such as carbon monoxide. The LANZATECH Process (Available from LanzaTech Inc., Parnell Auckland, New Zealand) uses microbial gas fermentation to convert any carbon monoxide containing gases produced by industries such as steel manufacturing, oil refining and chemical production, as well as gases generated by gasification of forestry and agricultural residues, municipal waste, and coal into valuable fuel and chemical products to produce ethanol and other molecules, such as 2,3-butanediol. A description of the LANZATECH microbial gas fermentation process is disclosed in U.S. Publication No. US20100323417 and in U.S. Pat. No. 8,119,378, which are hereby incorporated by reference.

Because the ethanol and associated oxygenates such as isopropanol, 2,3-butanediol, and other diols, including propanediols, and acids such as acetic acid are produced in very dilute concentrations in aqueous streams, recovery of the ethanol and some of the major oxygenated organic compounds by conventional means such as distillation and crystallation has been hindered by the large energy requirement to concentrate and separate the ethanol and associated oxygenates from the water.

The seeming disadvantage of the dilute ethanol in the aqueous fermentation stream became an advantage for the use of simulated moving bed technology to concentrate the ethanol in the aqueous fermentation stream. It was surprisingly discovered that in order to obtain a balance of selectivity and recovery in the simulated moving bed system, the ethanol/oxygenate mixture in the aqueous fermentation stream, or SMB feed stream, was required to be diluted in aqueous media. One example of a typical associated oxygenate produced in fermentation processes is 2,3-butanediol. Preferably, in processing a fermentation broth or biomass effluent stream comprising ethanol and 2,3-butanediol, the SMB feed stream comprises an ethanol/2,3-butanediol mixture which is less than or equal to 15 weight percent of the ethanol and 2,3-butanediol in water. More preferably, the fermentation broth or biomass effluent stream comprises less than or equal to 6 weight percent of the ethanol and 2,3-butanediol in water. A further limitation is that the concentration of the 2,3-butanediol in the SMB feed stream is less than 2 wt-%.

The SMB feed stream will also comprise biomass soluble proteins which were produced in the fermentor. Some of these biomass proteins or salts thereof may be recovered from the effluent of the fermentor and returned to the fermentor to control the operation of the fermentor or recovery potentially valuable components. However, if these soluble proteins or salts thereof are permitted to enter the SMB zone, they may be deposited on the stationary phase adsorbent during regeneration. Therefore, it is important that at least a portion of the soluble proteins in the effluent from a fermentor either be removed by any conventional means, or that the SMB feed stream be denatured by any conventional means. Such denaturation steps include heating or by introducing an alcohol such as methanol to the neutralized feed stream to provide a denatured feed stream.

The SMB feed stream may also undergo a neutralization step to adjust the pH of the SMB feed stream to a pH between about 5 and about 10. Typically, an SMB feed stream derived from a fermentor zone processing biomass will comprise acetic acid and may have a pH less than about 5. By treating the SMB feed stream in a neutralization zone with a base, such as ammonia, a portion of the acetic will be converted to ammonium acetate. Thus, the degree or extent of neutralization will determine the presence of the amount of acetic acid or ammonium acetate in the SMB feed stream which will be processed in the SMB zone.

In order to minimize operating problems in the SMB adsorption zone related to the plugging of the adsorbent with soluble biomass material during the regeneration steps, it is required to filter the SMB feed stream in a suitable filter preferably having 5 micron filter media to avoid introducing suspended particles greater than about 5 microns into the SMB system. More preferably, the filter will have a filter size of from about 1 micron to about 5 microns.

SMB—Stationary Phase Selection

In a series of screening studies to identify and classify potential materials for use as the stationary phase, it was found that a fluorinated carbon adsorbent provided the desired separation level. That is, when the stationary phase was fluorinated carbon, the desired separation of ethanol from the impurities such as 2,3-butanediol could be achieved.

A series of experiments were performed to compare the use of fluorinated carbon stationary phase to an activated carbon stationary phase. The carbon stationary phase material was an activated carbon having a particle size of about 325 microns (44 mesh) as ORSNCB4GR (Available from Orochem Technologies, Inc., Lombard, Ill.), hereinafter referred to as E-325. The fluorinated carbon stationary phase materials evaluated were surface fluorinated carbon adsorbents as ORSNCB4FL5GR and ORSNCB4FL1 GR (Available from Orochem Technologies, Inc., Lombard, Ill.) and hereinafter referred to as FC-5, and FC-1, respectively. Each of these surface fluorinated carbon adsorbents were prepared by subjecting an activated carbon adsorbent at effective conditions in a fluorine atmosphere to displace at least a portion of the oxygen groups consisting of —COOH, —COO, —COH, and —C=O present on the activated carbon. FC-1 was subjected to a fluorine atmosphere at conditions effective to provide a fluoride content of about 1.5 wt-% fluoride. FC-5 was subjected to a fluorine atmosphere at conditions effective to provide a fluoride content of about 5.0 wt-% fluoride. The fluoride levels on the fluorinated carbon adsorbents were estimated based on the severity of the fluoridation conditions. The surface fluorinated carbon adsorbent was prepared by replacing the oxygenated species on the surface of an oxygenated or activated carbon adsorbent. Preferably, the fluorinated carbon adsorbent comprises from about 0.5 to about 5.0 weight percent fluorine. More preferably, the fluorinated carbon adsorbent comprises from about 1.5 to about 5.0 weight percent fluorine. The experiments were carried out as follows:

STATIONARY PHASE EXAMPLES

Stationary Phase Example 1

A glass column having an inside diameter of 10 mm and a length of 250 mm was packed with 11 grams of E-325 adsorbent of activated carbon. A feed stream comprising 1 vol-% ethanol in deionized water was passed to the column at a temperature of 25° C. at a flow rate of 2 mL per minute. Ethanol in the effluent was measured continuously by a Waters RI detector (Available from Waters Corporation, Milford, Mass.). At the point of ethanol breakthrough, 68 mL of volume had passed through the bed. The amount of ethanol adsorbed on the E-325 adsorbent was 0.68 grams, which represented an Adsorption ratio of 6.07 w/w.

Stationary Phase Experiments 2-4

According to the procedure described hereinabove in Stationary Phase Example 1, the breakthrough point, amount of ethanol adsorbed, and the adsorption ratio were determined for 2,3-butanediol on E-325, ethanol on FC-5, and 2,3-butanediol on FC-5. The results of Stationary Phase Experiments 1-4 are summarized in Table 1.

TABLE 1

Comparison of Activated Carbon an Fluorinated Carbon Stationary Phase Adsorbents for Ethanol and 2,3-butanediol

| | Experiment | | | |
|---|---|---|---|---|
| | 1 | 2 | 3 | 4 |
| Organic at 1 vol-% in water | Ethanol | 2,3-Butanediol | Ethanol | 2,3-butanediol |
| Adsorbent | E-325 | E-325 | FC-5 | FC-5 |
| Volume Passed at Breakthrough, mL | 68 | 108 | 106 | 188 |
| Amt of Organic Adsorbed, grams | 0.68 | 1.08 | 1.06 | 1.88 |
| Adsorption Ratio, (W/W) | 6.07 | 9.64 | 9.46 | 16.7 |

Based on the results of Stationary Phase Experiments 1-4, it was concluded that the fluorinated carbon adsorbent FC-5 adsorbed significantly more ethanol and 2,3-butanediol than conventional activated carbon as represented by the E-325 adsorbent. For ethanol adsorption, the E-325 conventional activated carbon had an Adsorption ratio of 6.07 (w/w) compared to the fluorinated carbon FC-5 which had an Adsorption ratio of 9.64 (w/w). Similarly, for 2,3-butanediol adsorption, the E-325 conventional activated carbon had an Adsorption ratio of 9.46 (w/w) compared to the fluorinated carbon FC-5 which had an Adsorption ratio of 16.7 (w/w).

Another stationary phase adsorbent with suitable selectivity and hydrophobicity for use in the SMB process of the present invention is a C18 surface modified silica gel. A 4.6 mm ID by 150 mm long column was packed with 5 micron C18 surface modified silica gel (RELIASIL 5 micron C18, available from Infochroma, Zug, Switzerland). Deionized water was used as the mobile phase at a flow rate of 0.5 mL/min. An RI detector (Available from Waters Corporation, Milford, Mass.) was used to monitor the effluent. Sample of methanol, ethanol and 2-proponal were injected in volumes of 10 μL after the column was allowed to equilibrate in 100 percent water. The following retention times in minutes were measured:

| Sample Desorbent | Retention Time, minutes |
|---|---|
| Methanol | 3.82 |
| Ethanol | 4.96 |
| 2-Propanol | 8.54 |

Based on these retention times over the C18 modified silica gel adsorbent it was determined that the modified C18 silica gel could function as the stationary phase adsorbent with desorbents of methanol, ethanol, or 2-propanol in the SMB process of the present invention. It is preferred that the C18 modified silica gel adsorbent have a particle size of from about 250 to about 400 microns and have a porosity of from about 60 to about 130 Angstroms. More preferably, the C18 modified silica gel adsorbent has a particle size of from about 250 to about 300 microns.

The stationary phase adsorbent of the present invention comprised particles of an average particle size of between 50 and 500 microns. Preferably, the particle size ranged from 250 microns to 400 microns, and more preferably, the average particle size ranged from 300 to 375 microns. The particles of the stationary phase are irregularly shaped or spherical, or mixtures of irregular shaped and spherical shaped particles.

The stationary phase adsorbent used in the SMB process of the instant invention has the following physical properties, as shown in Table 2.

TABLE 2

Physical Properties of FC Stationary Phase Adsorbent Particles

| Property | Unit | ORSNCB4GR Activated Carbon | FC-1 and FC-5 Fluorinated Carbon |
|---|---|---|---|
| Surface Area | m$^2$g | 1400 | 1400 |
| Moisture | wt-% | 5 Max | 5 Max |
| Apparent Density | Kg/m3 | 410-460 | 410-460 |
| Particle Size | mesh** | 40-50 | 40-50 |
| Fluorine*** | wt-% | — | 1.5 and 5.0 |
| Chloride* | mg/Kg | 3 | 3 |
| Copper* | mg/Kg | 5 | 5 |
| Zinc* | mg/Kg | 1 | 1 |

*By Acid Extraction
**375-300 microns
***Estimated based on level of Fluorination Desorbent A desorption analysis was carried out on the fluorinated carbon stationary phase to evaluate the performance of a 22 mm×300 mm column (having a 22 mm inside diameter and a length of 300 mm) filled with fluorinated carbon adsorbent FC-1. Initially, a 6 vol-% solution of ethanol in deionized water at a temperature of about 25° C. was passed through the 22 mm×300 mm column to fully saturate the ethanol on the adsorbent. The build-up of ethanol on the fluorinated carbon adsorbent is shown in Table 3, below:

TABLE 3

Saturation of Fluorinated Carbon Adsorbent FC-1 with Ethanol

| | | | Percentage | | |
|---|---|---|---|---|---|
| Vial # | Volume | Cumulative | MeOH | EtOH | Water |
| 3 | 20 | 60 | .55 | 5.3 | 94.0 |
| 4 | 20 | 80 | .01 | 25.3 | 74.6 |
| 5 | 20 | 100 | 1.14 | 76.9 | 21.8 |

After the ethanol was adsorbed on the 22 mm×300 mm column, a methanol flush was carried out with 100 vol-% methanol. The methanol flush was passed to the saturated 22 mm×300 mm column at 25° C. and vials of the effluent were collected and analyzed by high pressure liquid chromatography. The results of the methanol desorption are shown hereinbelow in Table 4 as a Methanol Flush Profile representing the point at which the ethanol is flushed from the column and replaced with 100 vol-% methanol.

TABLE 4

Methanol Flush Profile of Fluorinated Adsorbent FC-1

| | | Cum. | Percentage | | |
|---|---|---|---|---|---|
| Vial # | Volume | Volume | MeOH | EtOH | Water |
| 2 | 20 | 40 | 1.40 | 90.1 | 8.47 |
| 3 | 20 | 60 | 2.55 | 93.1 | 4.36 |
| 4 | 20 | 80 | 24.10 | 70.9 | 4.97 |
| 5 | 20 | 100 | 68.4 | 30.9 | 0.74 |
| 6 | 20 | 120 | 90.6 | 7.61 | 1.80 |
| 8 | 20 | 160 | 100.2 | 0.71 | 0 |
| 12 | 20 | 240 | 106.0 | 0.36 | 0 |

At the conclusion of the methanol flush procedure discussed hereinabove, the 22×300 mm column was first purged with nitrogen and then was heated to a temperature of 130° C. The column was then flushed with steam at a temperature of 140° C. and the condensate collected. Table 5 shows the results of the steam regeneration on the effluent from the column.

TABLE 5

Steam Regeneration of the Adsorbent Column of Fluorinated Adsorbent FC-1 After Methanol Purge

| Time | Vol. of Water Passed | Volume Collected | Cumulative Volume | Percentage MeOH |
|---|---|---|---|---|
| 7 | 4.5 | 1 | 1 | 34 |
| 10.5 | 5.5 | 1 | 2 | 7.7 |
| 12 | 6 | 1 | 3 | 1.5 |
| 9 | 5 | 1.5 | 4.5 | 0.2 |
| 10 | N/A | 4.5 | 9 | 0.1 |

Following the above regeneration, the 22×300 mm column filled with the regenerated fluorinated carbon stationary phase adsorbent FC-1 and was subjected to a second breakthrough analysis using a solution of 6 vol-% ethanol in deionized water, as described hereinabove. The results of the second breakthrough test indicated that the breakthrough of ethanol occurred at the same point, confirming that the above regeneration steps fully regenerated the column and returned the column to its initial condition. The results of the second breakthrough test are shown in Table 6, hereinbelow.

TABLE 6

Breakthrough of 6 vol-% Ethanol After Regeneration

| | | Cum. | Percentage | | |
|---|---|---|---|---|---|
| Vial # | Volume | Volume | MeOH | EtOH | Water |
| 1 | 50 | 50 | 23.4 | 0.17 | 76.4 |
| 2 | 50 | 100 | 12.7 | 0.33 | 86.9 |
| 3 | 35 | 135 | 4.40 | 0.30 | 95.3 |
| 4 | 15 | 150 | 1.64 | 0.51 | 97.9 |
| 5 | 15 | 165 | 1.09 | 1.15 | 97.8 |

Preferably, the desorbent is selected from the group consisting of methanol, ethanol, propanol, and methyl tertiary butyl ether. More preferably, the desorbent is methanol or ethanol. Most preferably, the desorbent is ethanol. Preferably, desorbent has a purity of greater than or equal to 95 percent by weight and remaining portion water. More preferably, the desorbent has a purity of greater than or equal to 97 percent by weight and remaining portion water. Most preferably, the desorbent has a purity of greater than or equal to 99 percent by weight and remaining portion water.

Based on the above analysis, a continuous simulated moving bed (SMB) process based on fluorinated carbon as the stationary phase, methanol or ethanol as desorbents and an isolated regeneration of the stationary phase by steam, hot gas, or hot water (at a regeneration temperature ranging from 80 to 140° C.) was developed for an 8 to 10 adsorbent bed SMB system comprising an SMB process with 1 to 4 adsorbent beds undergoing regeneration during the predetermined.

In a similar manner, methyl tertiary butyl ether (MTBE) was evaluated in a breakthrough test as described hereinabove using a 10 mm inside diameter by 250 mm in length packed with 9.2 grams of the FC-5 fluorinated adsorbent. After the column was saturated with deionized water, a 1 vol-% of MTBE in deionized water was injected at a rate of 2 mL/minute. MTBE in the effluent was measured continuously by a Waters RI detector (Available from Waters Corporation, Milford, Mass.). At the point of MTBE breakthrough, 248 mL of volume had passed through the bed. At breakthrough, the capacity of the FC-5 fluorinated adsorbent for the MTBE was 27 weight percent.

DETAILED DESCRIPTION OF THE DRAWINGS

The SMB system of the current invention was arranged for maximum selectivity. The simulated moving bed operation is achieved by use of a plurality of adsorbent beds connected in series and a complex valve system, whereby the complex valve system facilitates switching at regular intervals the feed entry in one direction, the mobile phase desorbent entry in the opposite direction, while changing the extract and raffinate takeoff positions as well. The SMB system is a continuous process. Feed enters and extract and raffinate streams are withdrawn continuously at substantially constant compositions. The overall operation is equivalent in performance to an operation wherein the fluid and solid are contacted in a continuous countercurrent manner, without the actual movement of the solid, or stationary phase adsorbent.

The operation of the SMB system is carried out at a constant temperature within the adsorbent bed. The feed stream is introduced and components are adsorbed and separated from each other within the adsorbent bed. A separate liquid, the mobile phase desorbent, is used to counter currently displace the feed components from the pores of the stationary phase adsorbent. During the SMB cycle of the present invention, adsorbent beds are advanced through a desorption zone, a rectification zone, an adsorption zone, and a regeneration zone. The description of the SMB cycle as a 2-3-3 cycle means that in the cycle, 2 adsorbent beds are in the rectification zone, 3 adsorbent beds are in the rectification zone, and 3 adsorbent beds are in the adsorption zone.

FIG. 1 shows an embodiment of the simulated moving bed SMB adsorption zone of the present invention based on an eight adsorbent bed arrangement. Adsorbent beds 101, 102, 103, 104, 105, 106, 107, and 108, containing a stationary phase adsorbent selected from the group consisting of a fluorinated carbon adsorbent, and a modified C18 silica gel are disposed in a serial configuration such that in accordance with a prearranged cycle, conduit 16 provides fluid communication between the bottom of adsorbent bed 101 with the top of adsorbent bed 102, conduits 18 and 22 provide fluid communication between the bottom of adsorbent bed 102 bed and the top of adsorbent bed 103, conduit 26 provides fluid communication between the bottom of adsorbent bed 103 with the top of adsorbent bed 104, conduit 28 provides fluid communication between the bottom of adsorbent bed 104 with the top of adsorbent bed 105, conduits 32 and 34 provide fluid communication between the bottom of adsorbent bed 105 with the top of adsorbent bed 106, conduit 36 provides fluid communication between the bottom of adsorbent bed 106 with the top of adsorbent bed 107, conduit 40 provides fluid communication between the bottom of adsorbent bed 108 with the top of adsorbent bed 108, and conduit 42 provides for the withdrawal of fluid from the bottom of adsorbent bed 108. According to the prearranged SMB cycle of the present invention, an SMB zone feed stream is passed to the SMB adsorption zone in line 30 and 34 to adsorbent bed 106. A raffinate stream is withdrawn from conduit 42, and an extract stream is withdrawn via conduits 18 and 20 from adsorbent bed 102. A desorbent stream selected from the group consisting of methanol, ethanol, and methyl tertiary-butyl ether (MTBE) is introduced to adsorbent bed 101 in conduit 10. The adsorbent beds 101-108 are indexed according to a 2-3-3 SMB cycle such that at least 2 adsorbent beds undergo desorption, at least 3 adsorbent beds undergo rectification, and at least 3 adsorbent beds undergo adsorption during the SMB cycle. The objective is to recover ethanol and 2,3-butanediol with some methanol in the extract. The extract should contain less than 0.5% moisture.

The raffinate from the SMB zone should contain only water because the raffinate is returned to the fermentation broth. In the above eight column system, when the desorbent is methanol, it is difficult to remove methanol from the raffinate. To assure the essentially complete removal of methanol from the raffinate, the methanol must be removed from the adsorbent bed before the adsorbent bed is moved to the position in the predetermined cycle were the raffinate is pushed out through that adsorbent bed. This further removal of desorbent from the raffinate can be accomplished by the addition of an isolated regeneration step to purge any residual desorbent from the adsorbent bed prior to the introduction of the desorbent to the SMB system.

Although not shown in FIG. 1, an SMB feed stream which is derived from a process such as a biomass fermentor will require pretreatment before being introduced to the SMB zone. This pretreatment will vary depending upon the objective of the overall complex. For example, biomass effluent may contain acidic species, such as acetic acid. Complete neutralization of the biomass effluent will convert the acetic acid to less valuable components. Thus, as a general rule, pretreatment by neutralization of the biomass effluent will be carried out only to the degree necessary to protect the stationary phase adsorbent while retaining as much of the valuable acetic acid species as required.

A typical biomass product stream comprises water, ethanol, and butanediol and will also include acetic acid, and soluble biomass. In one pretreatment scheme, optionally, the biomass stream will be passed to a neutralization zone to provide an at least partially neutralized feed stream having a pH of from about 5 to less than about 10. Such neutralization will convert at least a portion of any acetic acid in the biomass stream to ammonium acetate. If acetic acid is to be recovered as a product in a downstream step, neutralization will only be performed to the degree required to meet the minimum pH requirements. Following neutralization, the neutralized feed stream is passed to a denaturation zone wherein the neutralized stream will be denatured in a conventional manner, by heating or by introducing an alcohol such as methanol to the neutralized feed stream to provide a denatured feed stream. The denatured feed stream is passed to a filtration zone to filter the denatured feed stream in a filter which has a filter size of from about 1 to about 5 microns to provide a filtered feed stream.

The filtered feed stream is an aqueous stream which preferably comprises less than about 15 wt-% ethanol and butanediol combined. More preferably, the filtered feed stream comprises less than about 10 wt-% ethanol and butanediol combined. Preferably, the filtered feed stream comprises between about 3 wt-% to about 10 wt-% ethanol, and more preferably, the filtered feed stream comprises between about 3 to about 9 wt-% ethanol. Preferably, the filtered feed stream comprises between about 0.1 to about 5 wt-% 2,3-butanediol, and more preferably, the filtered feed stream comprises between about 0.5 to about 3 wt-% 2,3-butanediol.

In the embodiment of the present invention according to FIG. 1, when the filtered feed stream introduced to the SMB zone in conduit 30 contained 6 wt-% ethanol and 3 wt-% 2,3-butanediol, the desorbent is 99 vol-% methanol, and the stationary phase adsorbent was a fluorinated carbon adsorbent, the extract stream in conduit 20 was essentially free of water, and the raffinate stream in conduit 42 was essentially free of either ethanol or 2,3-butanediol. In the extract stream, by the term essentially free of water it is meant that the stream contained less than 5 wt-%, and more preferably less than 1 wt-% of water. Similarly, in the raffinate stream, by the term essentially free of water it is meant that the stream contained less than 5 wt-%, and more preferably less than 1 wt-% of ethanol and 2,3-butanediol. The raffinate stream in conduit 42 comprised about 69 wt-% methanol and the remainder was water. The raffinate stream in line 42 was passed to a methanol stripping zone (not shown) to recover the methanol for return of the methanol to the SMB zone as the mobile phase desorbent. The water stripped from the raffinate stream was returned to the fermentor (not shown). The extract stream in conduit 20, comprised about 5 to 10 wt-% of both ethanol and 2,3-butanediol in methanol, and essentially no water. The extract stream was passed to a separation zone (not shown) to separate the ethanol and the 2,3-butanediol. Thus, the operation of the SMB zone in the 2-3-3 configuration of the present invention provided a 95 plus percent yield of ethanol and 2,3-butanediol with a 95 plus percent recovery.

Figure 2:
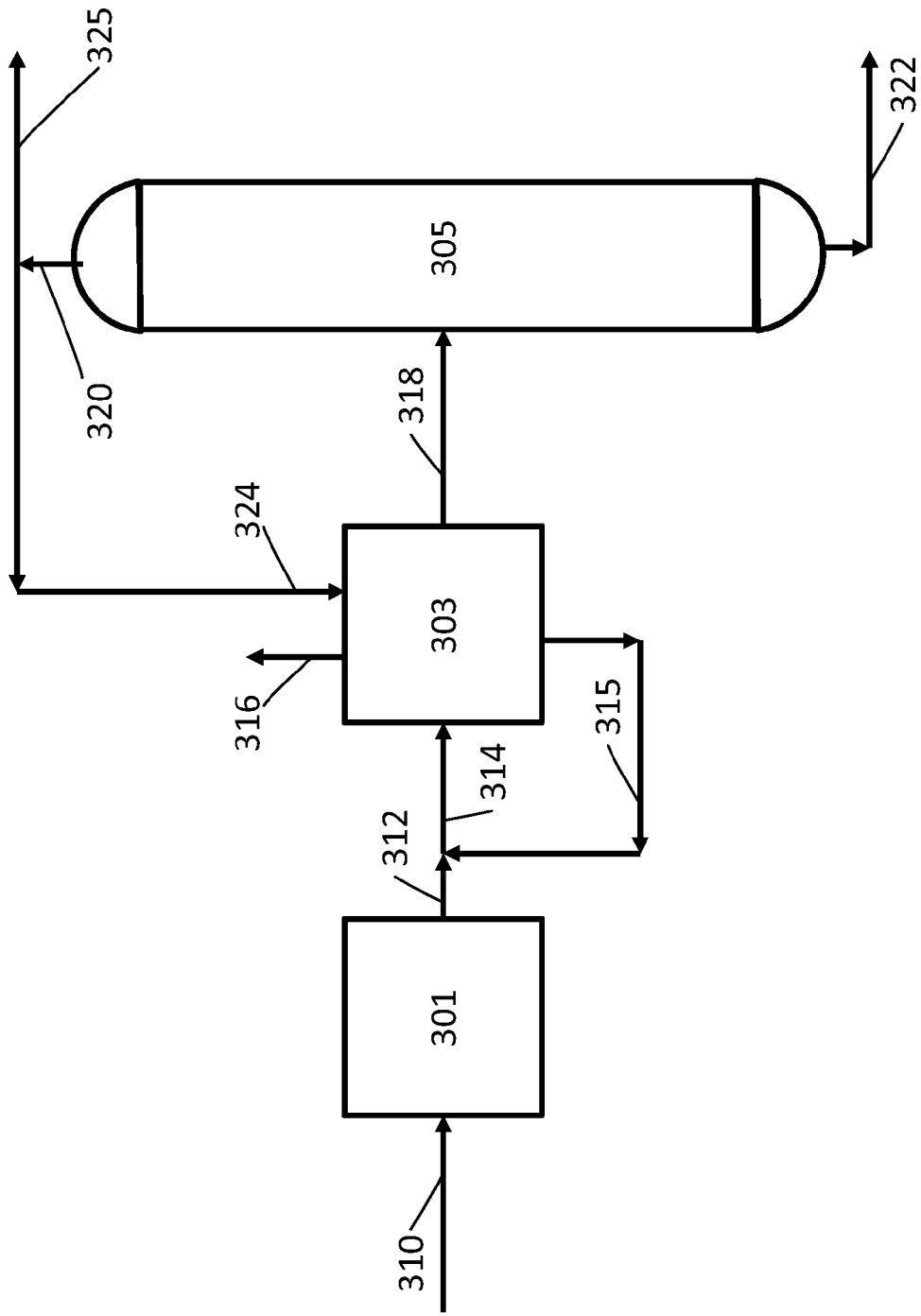
FIG. 2 is a schematic process flow diagram representing an embodiment of the present invention for a simulated moving bed adsorption process for the dewatering of ethanol combined with a pretreatment step and a downstream ethanol/butanediol separation.

FIG. 2 shows an embodiment of the invention with the SMB zone 303 in a complex additionally comprising a pretreatment zone 301 and an ethanol/butanediol separation zone 305. A biomass effluent such as a fermentation broth or feed stream from a fermentor (not shown) in line 310 comprising water, ethanol, butanediol, acetic acid, and soluble biomass is passed to the pretreatment zone 301. The pretreatment zone consists of a neutralization zone, a denaturation zone, and a filtration zone. In the pretreatment zone 301, the feed stream optionally is passed to a neutralization zone (not shown) wherein the feed stream is at least partially neutralized to provide a neutralized feed stream having a pH of between about 5 and about 10 to provide a neutralized feed stream comprising water, ethanol, butanediol, acetic acid, ammonium acetate, and soluble biomass salts. The amount of acetic acid remaining in the neutralized feed stream will depend on the degree of neutralization. The more ammonium acetate produced by the neutralization, the less acetic acid will remain in the neutralized feed stream. The neutralized feed stream is passed to a denaturation zone (not shown) wherein the neutralized feed stream is denaturated in any conventional manner such as heating or adding additives or solvents to provide a denaturated feed stream. The denaturated feed stream is passed to a filtration zone (not shown) wherein the denatured feed stream is filtered in a filter having a filter size of from about 1 micron to about 5 microns to provide a filtered feed stream in line 312. The filtered feed stream in line 312 is passed via conduits 312 and 314 to an SMB adsorption zone 303. The SMB zone 303 is further described in FIG. 3. The SMB zone 303 employs ethanol as a desorbent. A raffinate stream comprising water and ammonium acetate is withdrawn from the SMB zone 303 in line 316 and returned to the fermentor (not shown). The extract stream in line 318 is withdrawn from the SMB zone 303 and passed to the ethanol/butanediol separation zone 305. In the ethanol/butanediol separation zone 305, a column overhead stream in line 325 comprising ethanol is recovered as an ethanol product stream via lines 320 and 325, and a butanediol product stream is withdrawn from the bottom of the ethanol/butanediol separation zone 305 in line 322. At least a portion of the column overhead stream in line 320 is returned to the SMB zone 303 via line 324 to be used as desorbent. The ethanol/butanediol separation zone 305 is a conventional distillation column having about 20 theoretical plates and operating at a temperature of between about 78° C. and about 210° C.

Figure 3:
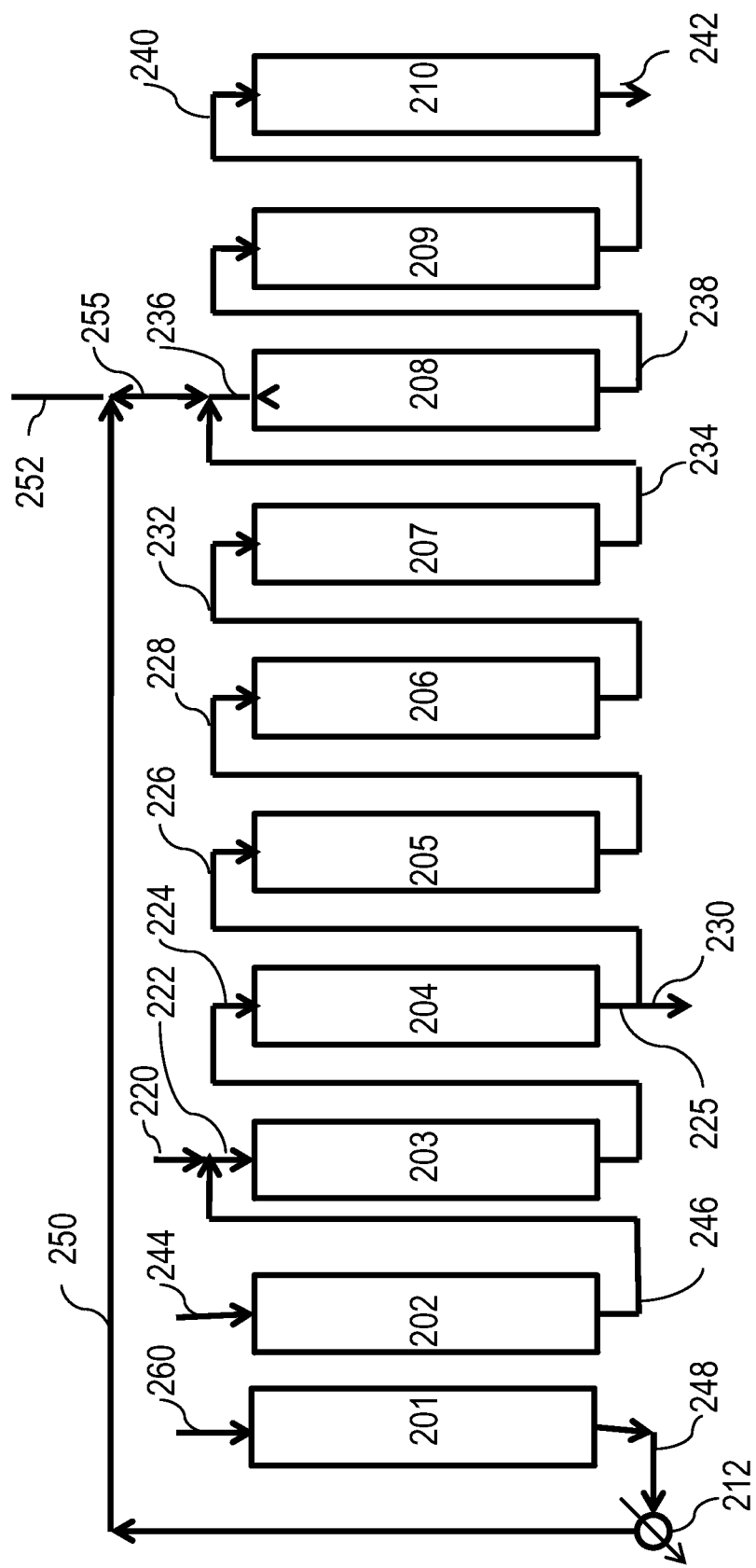
FIG. 3 is a schematic process flow diagram representing an embodiment of the present invention for a simulated moving bed adsorption process employing 10 adsorption beds wherein two adsorption beds undergo regeneration.

FIG. 3 shows an embodiment of the simulated moving bed SMB adsorption zone of the present invention based on a ten adsorbent bed SMB adsorption zone, wherein two adsorbent beds are undergoing an isolated regeneration in each cycle in conjunction with an eight adsorbent bed arrangement similar to the SMB arrangement in FIG. 1. All of the adsorbent beds contain a stationary phase adsorbent selected from the group consisting of fluorinated carbon adsorbent and a modified C18 silica gel. Referring to FIG. 3, adsorbent beds 201 and 202 are separately undergoing an isolated regeneration. In regeneration, a low pressure steam stream at a steam temperature of between about 100° C. and 120° C. is passed to the top of adsorbent bed 201 to desorb residual ethanol in line 248, which is subsequently condensed by condenser 212 to a condenser temperature of between about 20° C. to about 40° C. to provide a liquid condensate stream comprising water and desorbed ethanol. The liquid condensate stream in line 250 is combined with the filtered feed stream in line 252 and passed to adsorbent bed 208 via lines 255 and 236. A hot gas stream comprising carbon dioxide, nitrogen, and water, such as a combustion gas or a vent gas stream from a fermentor (not shown), at a hot gas temperature of between about 80° C. to about 120° C. is passed to the top of column 202 to purge the non-selective pore volume of the adsorbent bed and recover a purged liquid stream comprising ethanol in line 246 and combining the purged liquid stream with a desorbent stream 220 being ethanol before passing the desorbent stream to the top of adsorbent bed 203. The Adsorbent beds 203, 204, 205, 206, 207, 208, 209, and 210 are disposed in a serial configuration such that in accordance with a prearranged cycle, conduit 224 provides fluid communication between the bottom of adsorbent bed 203 with the top of adsorbent bed 204, conduits 225 and 226 provide fluid communication between the bottom of adsorbent bed 204 bed and the top of adsorbent bed 205, conduit 228 provides fluid communication between the bottom of adsorbent bed 205 with the top of adsorbent bed 206, conduit 232 provides fluid communication between the bottom of adsorbent bed 206 with the top of adsorbent bed 207, conduits 234 and 236 provide fluid communication between the bottom of adsorbent bed 207 with the top of adsorbent bed 208, conduit 238 provides fluid communication between the bottom of adsorbent bed 208 with the top of adsorbent bed 209, conduit 240 provides fluid communication between the bottom of adsorbent bed 209 with the top of adsorbent bed 210, and conduit 242 provides for the withdrawal of fluid from the bottom of adsorbent bed 210. The SMB zone is operated at an SMB pressure of about 100 psig (6.8 barg) and an SMB temperature of between about 30° C. and about 35° C. According to the prearranged SMB cycle of the present invention, an SMB zone feed stream is passed to the SMB adsorption zone in line 220 and 222 to adsorbent bed 203. A raffinate stream is withdrawn from conduit 242, and an extract stream is withdrawn via conduits 225 and 230 from adsorbent bed 204. The desorbent stream 220 comprising ethanol is introduced to adsorbent bed 203 in conduit 220. The adsorbent beds 201-210 are indexed according to a 2-3-3-2 SMB cycle such that at least 2 adsorbent beds undergo desorption, at least 3 adsorbent beds undergo rectification, and at least 3 adsorbent beds undergo adsorption, and 2 beds undergo isolated regeneration during the SMB cycle. The extract steam in conduit 230 to passed to a recovery zone for the separation of ethanol and 2,3-butanediol, and the raffinate stream is returned to the fermentor zone as recycle water. If the desorbent is other than ethanol, such as methanol, propanol, or MTBE, the purged desorbent stream in line 250 would not be recombined with the feed stream.

Figure 4:
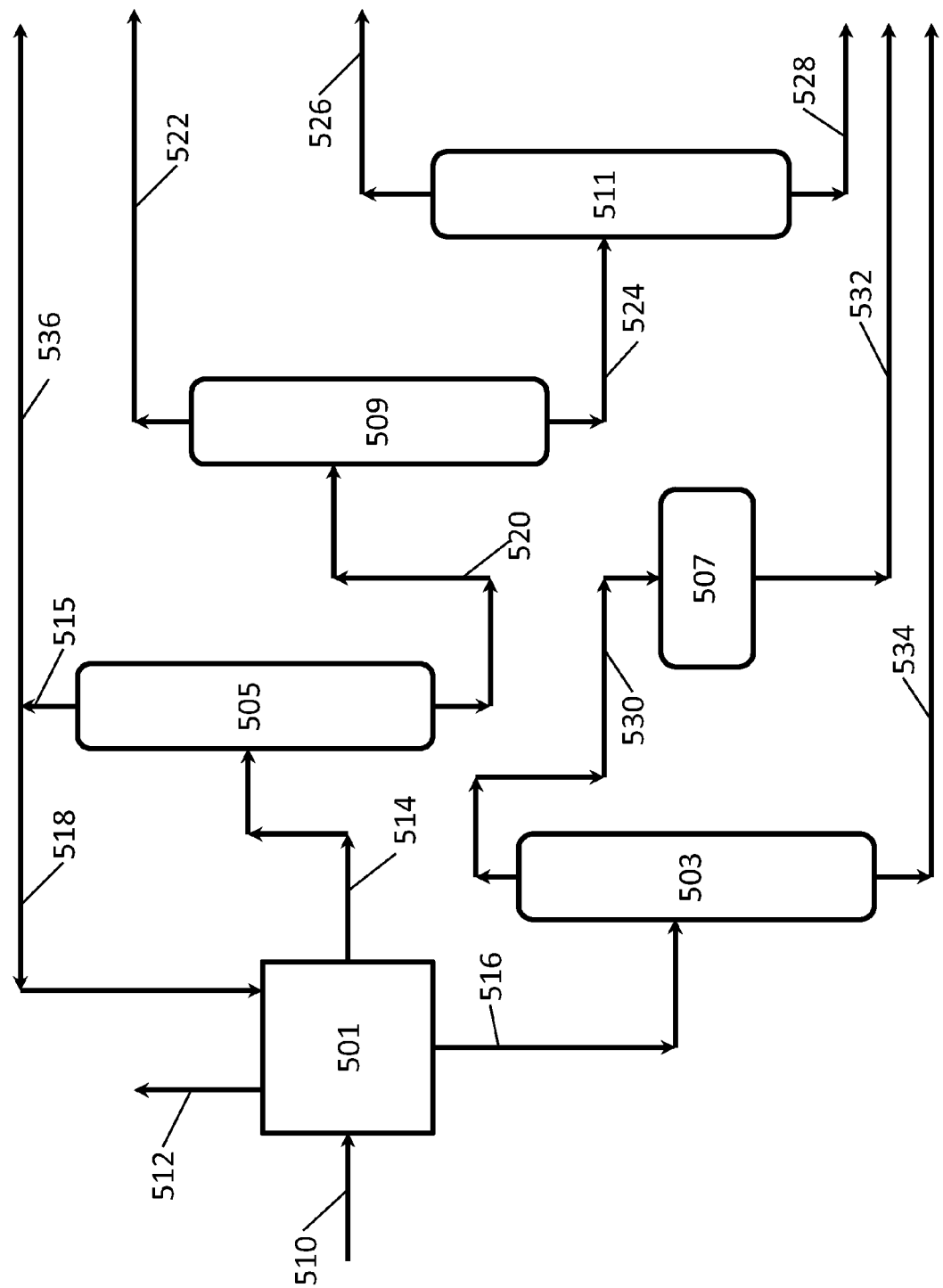
FIG. 4 is a schematic process flow diagram representing a conventional scheme for recovery of ethanol from a fermentation stream following stripping with a portion of the vent gas stream from the fermentation zone, without recovery of 2,3-butanediol.

FIG. 4 is a schematic process flow diagram of a another embodiment of the present invention showing the integration of the SMB zone 501 (with reference to the SMB scheme described herein above in FIG. 3) in combination with the recovery of fuel ethanol in line 532 and 2,3-butandiol in line 526. A feed stream comprising water, ethanol, acetic acid, 3,4-butanediol, and soluble biomass derived from a biomass fermentor having been pretreated as described hereinabove by denaturation and filtration, but without neutralization is passed in line 510 to the SMB zone 501 to provide an extract stream in line 514 comprising ethanol, acetic acid, 3,4-butanediol, and soluble biomass. The extract stream in line 514 is passed to an ethanol/butanediol separation zone 505 to provide a recycle ethanol stream via lines 515 and 518 and an acetic acid/butanediol stream comprising acetic acid, 2,3-butanediol, and soluble biomass in line 520. Alternatively, a portion of the recycle ethanol stream may be recovered as a secondary ethanol product stream via lines 515 and 536. The acetic acid/butanediol stream in line 520 is passed to an acetic acid recovery column 509 to separate the acetic acid from the butanediol to provide an acetic acid stream in line 522 and a butanediol rich stream in line 524. The butanediol rich stream in line 524 is passed to a butanediol recovery column to 511 to provide a 2,3-butanediol product stream in line 526, and a soluble biomass stream in line 528. The raffinate stream in line 516 is withdrawn from the SMB zone 501 comprises ethanol and water and is passed to an ethanol/water separation column 503 to provide an ethanol product stream in line 530 and a water stream in line 534. The ethanol product stream in line 530 is passed to a conventional ethanol dryer 507 to provide a fuel grade ethanol stream in line 532.

Figure 5:
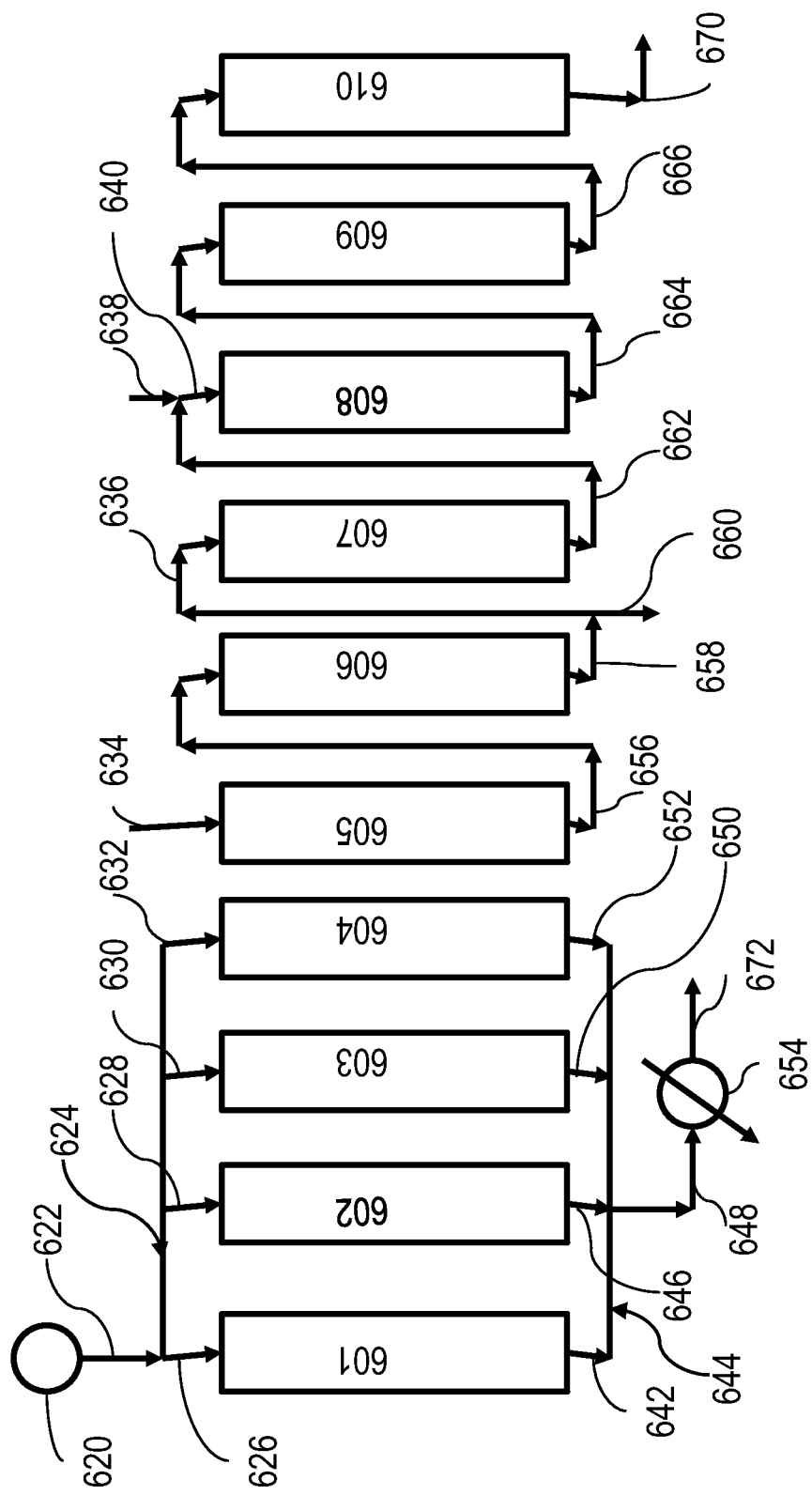
FIG. 5 is a schematic process flow diagram representing an embodiment of the present invention for a simulated moving bed adsorption process illustrating the separate recovery of a fuel grade ethanol product, 2,3-butanediol, and a soluble biomass stream.

FIG. 5 shows a still further embodiment of the simulated moving bed SMB adsorption zone of the present invention based on a ten adsorbent bed SMB adsorption zone, wherein four adsorbent beds are undergoing regeneration with hot gas or hot water in each cycle in conjunction with a ten adsorbent bed arrangement. According to FIG. 6, according to a prearranged cycle, four of the adsorbent beds (601, 602, 603, and 604) undergo regeneration per cycle. The regeneration comprises passing a hot gas stream, 620, such as a vent gas at a hot gas temperature of between about 100 and about 140° C. The hot gas stream comprises carbon oxides, nitrogen, methane, and hydrogen in line 622 to a hot regeneration header 624. Preferably, the effective regeneration conditions include a regeneration temperature of between about 80° C. and about 140° C. More preferably, the effective regeneration conditions include a regeneration temperature of between about 80° C. and about 100° C. Separately and simultaneously in lines 626, 628, 630, and 632 to the top of adsorbent beds 601, 602, 603, and 604, respectively. Simultaneously and separately withdrawing regeneration effluent in lines 642, 646, 650, and 652 from the bottom of adsorbent beds 601, 602, 603, and 604, respectively, to a regeneration effluent header 644, to provide a collected regeneration effluent. The collected regeneration effluent is passed from the regeneration header in line 648 to a chiller 654 to provide a chilled regeneration effluent stream in line 672. The chiller is operated at a temperature and pressure which is effective to liquefy any desorbed methanol from the adsorbent beds 601, 602, 603, and 604. The chilled regeneration effluent stream 672 is passed to a methanol recovery zone (not shown) for the recovery of methanol in a conventional manner by stripping or distillation for use in the SMB process as desorbent. Returning to FIG. 6, a desorbent such as methanol, ethanol, or MTBE is passed to the top of adsorbent bed 605, a feed stream is introduced to adsorbent bed 608 via lines 638 and 640, and a raffinate stream 670 is withdrawn in line 670. Line 656 provides fluid communication between the bottom of adsorbent bed 605 and the top of adsorbent bed 606; lines 658 and 636 provide fluid communication between the bottom of adsorbent bed 606 and the top of adsorbent bed 607; lines 662 and 640 provide fluid communication between the bottom of adsorbent bed 607 and the top of adsorbent bed 608; line 664 provides fluid communication between the bottom of adsorbent bed 608 and the top of adsorbent bed 609; and, line 666 provides fluid communication between the bottom of adsorbent bed 609 and the top of adsorbent bed 610.

Figure 6:
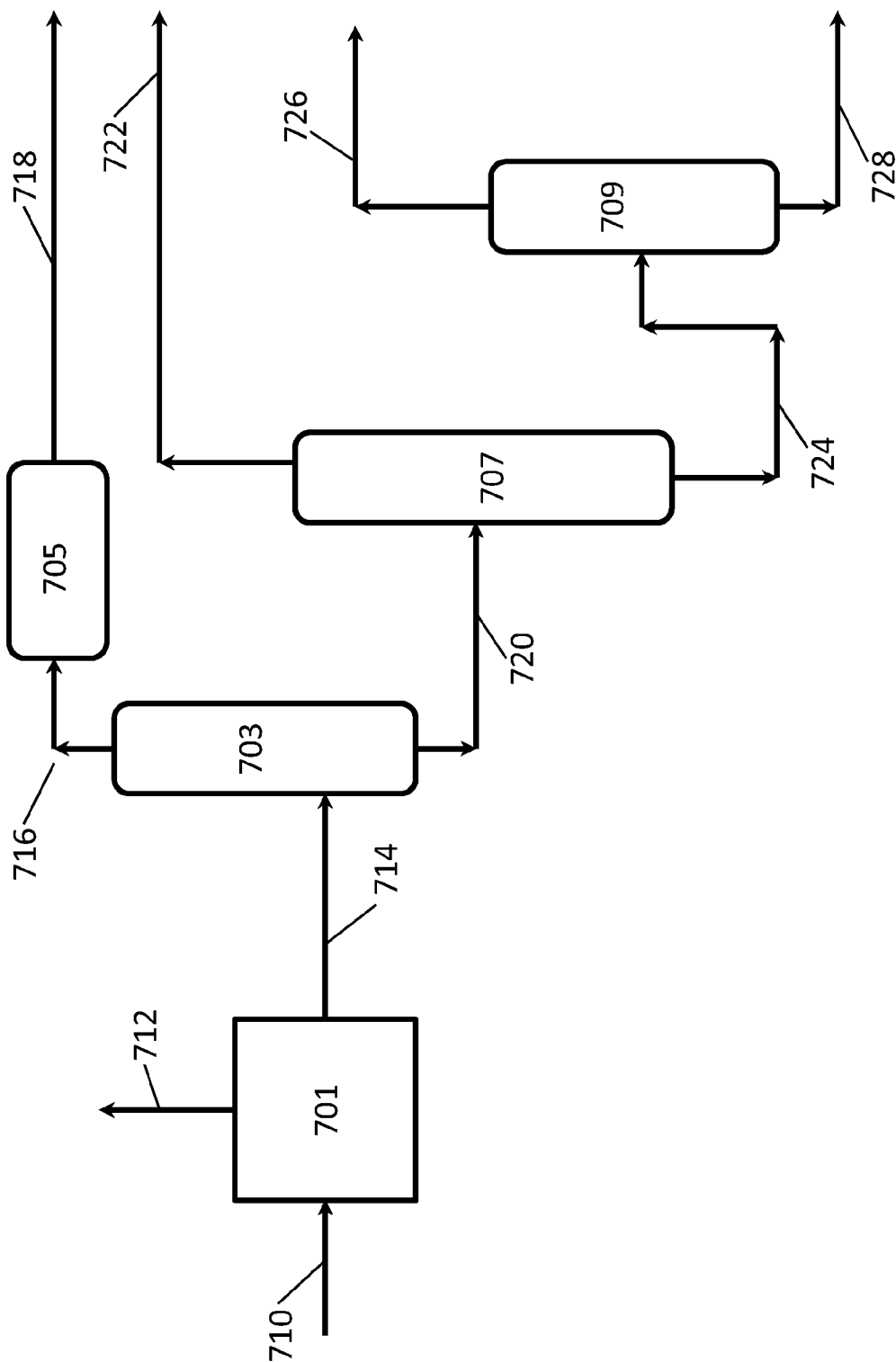
FIG. 6 is a schematic process flow diagram representing an embodiment of the present invention for a simulated moving bed adsorption process illustrating employing 10 adsorbent beds wherein four beds per cycle undergo regeneration.
Figure 7:
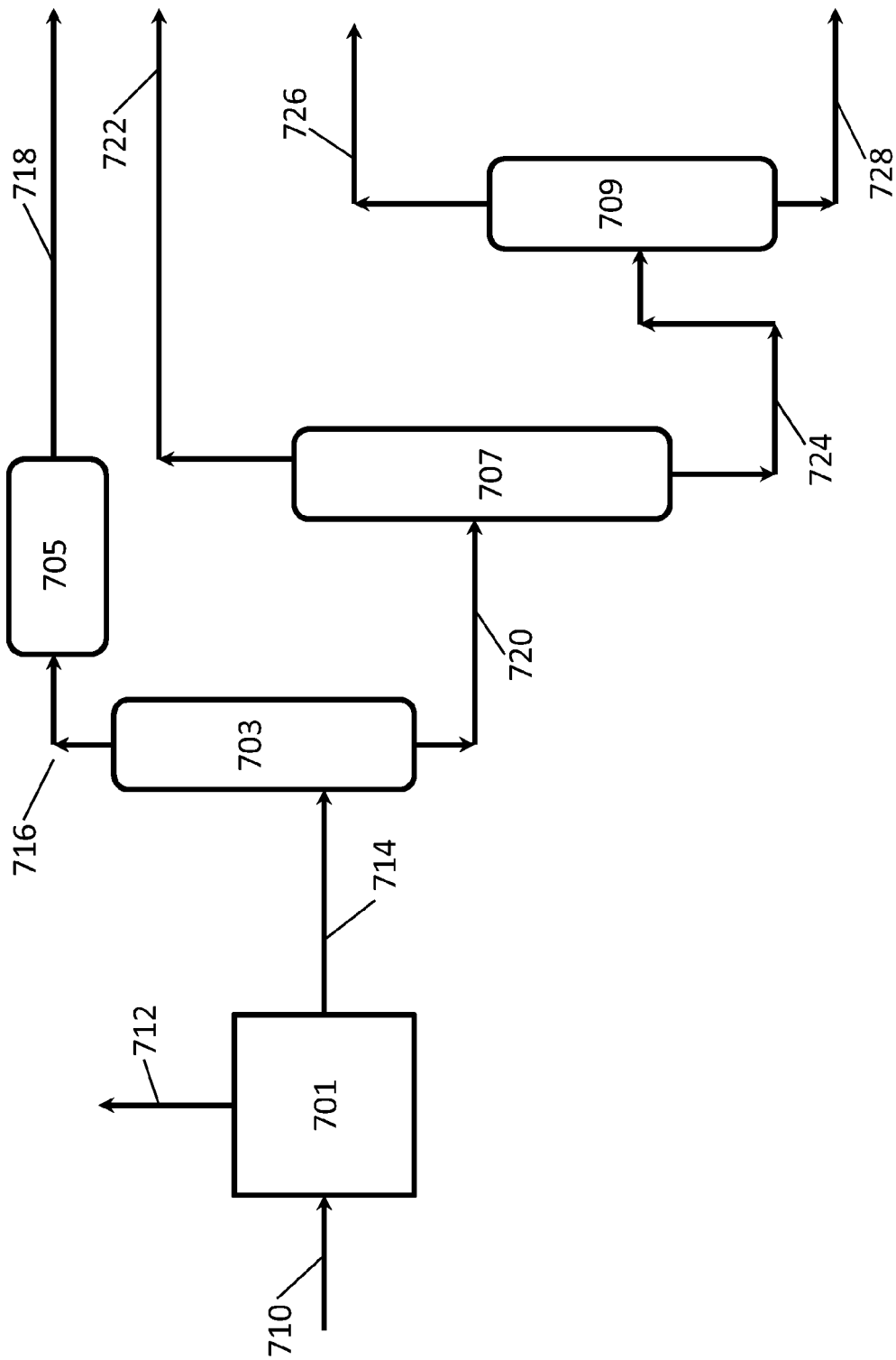
FIG. 7 is a schematic process flow diagram representing an embodiment of the present invention for a simulated moving bed adsorption process illustrating the separate recovery of a fuel grade ethanol product, 2,3-butanediol, and a soluble biomass stream wherein the fermentation stream does not comprise acetic acid.

FIG. 6 is a schematic process flow diagram of a another embodiment of the present invention showing the integration of the SMB zone employing desorbent in the SMB zone 701 as described in FIG. 3 hereinabove. A feed stream comprising water, ethanol, acetic acid, 3,4-butanediol, and soluble biomass derived from a biomass fermentor having been pretreated as described hereinabove by neutralization, denaturation and filtration is passed in line 710 to the SMB zone 701 to provide an extract stream in line 714 comprising water, ethanol, ammonium acetate, 3,4-butanediol, and soluble biomass, and a raffinate stream in line 712, comprising water. The extract stream in line 714 is passed to an ethanol stripping zone to provide an overhead ethanol stream in line 716 comprising ethanol and water and a stripper bottoms stream in line 720 comprising water, ethanol, ammonium acetate, 3,4-butanediol, and soluble biomass. The overhead ethanol stream is passed to an ethanol dryer 705 to provide a fuel grade ethanol stream in line 718 comprising ethanol and less than 100 ppm water. The stripper bottoms stream in line 720 is passed to a water recovery zone 707 to provide an recovered water stream in line 722, and butanediol rich stream in line 724. The butanediol rich stream in line 724 is passed to a butanediol column to provide a 2,3-butanediol product stream in line 726 and a soluble biomass stream in line 728.

The present invention is further described and illustrated by the following examples.

Material Balance Example

SMB Using Ethanol Desorbent

With reference to the process flow scheme shown in FIG. 2, the following material balance was developed for a 65000 MTA ethanol recovery plant using a 10 adsorbent bed SMB complex with ethanol as the desorbent and a stationary phase comprising fluorinated carbon. An actual fermentation broth from a biomass fermentor or feed stream had the following composition:

Composition of Fermentation Broth

|  | Flow Rate, Kg/Hr |
|---|---|
| Compound: | |
| Acetic Acid | 1225 |
| Biomass Soluble | 735 |
| Ammonium acetate | 613 |
| Ethanol | 10294 |
| 2,3-Butanediol | 4412 |
| Water, L/Hr | 204248 |
| Conditions: | |
| Temperature, ° C. | 35 |
| pH | 5.1-5.3 |

Following pretreatment comprising neutralization, denaturation and filtration, the filtered feed stream has the following character:

|  | Flow Rate, Kg/Hr |
|---|---|
| Compound: | |
| Acetic Acid | 0 |
| Biomass Soluble | 0 |
| Ammonium acetate | 2450 |
| Ethanol | 10294 |
| 2,3-Butanediol | 4412 |
| Water, L/Hr | 204248 |
| Conditions: | |
| Temperature, ° C. | 35 |
| pH | 7.0 |

The SMB operation using the 2-3-3-2 configuration described in FIG. 3 with 2 adsorbent beds being regenerated in each cycle, with a fluorinated carbon stationary phase, and pure ethanol as the desorbent, produced a raffinate stream with the following composition:

| Compound: | Flow Rate, Kg/Hr |
|---|---|
| Ammonium acetate | 2450 |
| Water, L/Hr | 192943 |

An extract stream with the following composition:

| Compound: | Flow Rate, Kg/Hr |
|---|---|
| 2,3-Butanediol | 4412 |
| Ethanol | 192943 |

The extract stream was passed to a separation zone which separated the ethanol from the 2,3-butanediol providing 4412 Kg/Hr of 2,3-butanediol, and a combined ethanol stream of 30880 Kg/Hr, of which 10294 Kg/Hr was recovered as an ethanol product stream, and 20586 Kg/Hr of the combined ethanol stream was returned to the SMB zone as recycle ethanol for use as desorbent.

While the disclosure has been described in terms of specific embodiments, it is evident in view of the foregoing description that numerous alternatives, modifications and variations will be apparent to those skilled in the art. Accordingly, the disclosure is intended to encompass all such alternatives, modifications and variations which fall within the scope and spirit of the disclosure and the following claims.

We claim:

1. A continuous SMB process for the recovery of ethanol from a biomass effluent stream from a fermentor, said biomass effluent stream comprising water, ethanol, at least one associated oxygenate, acetic acid, and suspended solids, wherein said SMB process having a desorption zone, a rectification zone, an adsorption zone, and a regeneration zone as SMB zones, wherein each SMB zone has an upper portion and a bottom portion and wherein the desorption zone, the rectification zone, the adsorption zone and the regeneration zone, each comprise one or more serially-linked adsorbent beds and each adsorbent bed containing a stationary phase adsorbent selective for the adsorption of ethanol and said associated oxygenate, said SMB process comprising:
   a. passing the biomass effluent stream to a pretreatment zone comprising a denaturation zone and a filtration zone and in the denaturation zone denaturating the biomass effluent stream to provide a denaturated biomass effluent stream and in the filtration zone filtering the denaturated biomass effluent stream through a filter having a filter size of less than or equal to 5 microns and adjusting pH to between about 5 and about 10 to provide a treated biomass effluent stream comprising water, at least one associated oxygenate, acetic acid and soluble biomass;
   b. introducing the treated biomass effluent stream having a concentration of ethanol and the associated oxygenate being less than about 15 wt-% in water to the upper portion of the adsorption zone and withdrawing a raffinate stream comprising water and a minor portion of ethanol from the bottom portion of the adsorption zone;
   c. passing a desorbent stream in a desorbent flow direction to the upper portion of the desorption zone and withdrawing a desorbent zone effluent stream from the bottom of the desorption zone and recovering a portion of the desorption effluent stream as an extract stream comprising ethanol, said associated oxygenate, acetic acid and a minor portion of water;
   d. passing a remaining portion of the desorption effluent stream to the upper portion of the rectification zone and withdrawing a rectification zone effluent;
   e. combining the rectification zone effluent with the treated biomass effluent stream prior to introducing the treated biomass effluent stream to the upper portion of the adsorption zone;
   f. isolating a regeneration zone and passing a hot regeneration stream at a regeneration temperature to the upper portion of the regeneration zone and withdrawing a spent regeneration stream from the bottom portion of the regeneration zone and cooling the spent regeneration stream to provide a cooled spent regeneration stream;
   g. passing the extract stream to a recovery zone to provide an ethanol product stream and an associated oxygenate product stream; and,
   h. indexing the adsorbent beds sequentially in a direction which is counter current to the desorbent flow direction.

2. The process of claim 1, wherein the stationary phase adsorbent is selected from the group consisting of fluorinated carbon and modified C18 silica gel.

3. The process of claim 1, wherein the desorbent is selected from the group consisting of methanol, ethanol, propanol, and methyl tertiary butyl ether.

4. The process of claim 1, wherein the desorbent is ethanol.

5. The process of claim 1, wherein the hot regeneration temperature ranges from about 80° C. to about 120° C.

6. The process of claim 1, wherein the regeneration stream is selected from the group consisting of a gas stream, steam, water, and ethanol.

7. The process of claim 1, wherein the regeneration stream is a vent gas or combustion gas comprising methane, nitrogen, carbon oxides and hydrogen.

8. The process of claim 1, wherein the at least one associated oxygenate is selected from the group consisting of isopropyl alcohol (IPA), butanol (BuOH), n-butanol, t-butanol, hydroxymethyl-tetrahydrofuran or tetrahydro-2-furfuryl alcohol (THFA), 1,2-propanediol, 1,3-propanediol, 1,2-butanediol, 1,3-butanediol, 1,4-butanediol, 2,3-butanediol, 1,2-pentanediol, 1,5-pentanediol, 1,8-octanediol, etohexadiol, p-menthane-3,8-diol, 2-methyl-2,4-pentanediol, propanal, butanal, 2,5-furan-diacrboxyaldehyde, acetic acid, oxopropanoic acid, acrylic acid, levulinic acid, succinic acid, 2,5-furan-dicarboxylic acid, aspartic acid, glucaric acid, glutamic acid, itaconic acid, acetylacrylic acid, 4-O-Me-glucuronic acid, gluconic acid, and xylonic acid.

9. The process of claim 1, wherein the at least one associated oxygenate is 2,3-butanediol.

10. The process of claim 1, wherein the desorbent is ethanol and further comprising combining the cooled spent regeneration stream with the treated biomass effluent stream prior to introducing the treated biomass effluent stream to the upper portion of the adsorption zone.

11. The process of claim 1, further comprising reducing or removing acetic acid from the treated biomass effluent stream prior to step (a).

12. The process of claim 9, further comprising passing the raffinate stream to an ethanol water separation column to provide a recycle ethanol stream and heating and returning the recycle ethanol stream to the regeneration zone as the hot regeneration stream.

13. The process of claim 1, wherein the minor portion of water in the extract stream is less than 5 vol-%.

14. The process of claim 1, wherein the minor portion of ethanol in the raffinate stream is less than 5 vol-%.

15. The process of claim 1, further comprising passing the ethanol product stream to an ethanol dryer to provide a fuel grade ethanol stream.

16. A process for the recovery of ethanol from a biomass effluent stream comprising water, ethanol, 2,3-butanediol, acetic acid and soluble biomass, said process comprising:
   a. passing the biomass effluent stream to a pretreatment zone comprising a denaturation zone and a filtration zone and in the denaturation zone denaturing the biomass effluent stream to provide a denatured biomass effluent stream and in the filtration zone filtering the denatured biomass effluent stream through a filter having a filter size of less than or equal to 5 microns and adjusting pH to between about 5 and about 10 to provide a treated biomass effluent stream comprising water, at least one associated oxygenate, acetic acid and soluble biomass;
   b. passing the treated biomass effluent stream having a concentration of ethanol and 2,3-butanediol being between about 6 wt-% and less than about 15 wt-% in water to a simulated moving bed adsorption zone having a plurality of adsorbent beds containing a stationary phase adsorbent selected from the group consisting of a fluorinated carbon adsorbent and a modified C18 silica gel, and a mobile phase desorbent selected from the group consisting of methanol, ethanol, and methyl tertiary-butyl ether (MTBE), wherein at least one adsorbent bed is regenerated at effective regeneration conditions with a regeneration stream selected from the group consisting of methanol, ethanol, hot water, steam, a vent gas stream, and combinations thereof to provide a raffinate stream comprising the mobile phase desorbent and water and an extract stream comprising ethanol, 2,3-butanediol, and dissolved solids, said extract stream being essentially free water;
   c. passing the raffinate stream to a stripping zone to strip at least a portion of the desorbent from the water to provide a recovered desorbent stream and a waste water stream, and returning at least a portion of the recovered desorbent stream to the SMB zone as the desorbent stream; and,
   d. passing the extract stream to a recovery zone to provide an ethanol stream and a butanediol stream.

17. The process of claim 16, wherein the filtered feed stream has a concentration of ethanol and 2,3-butanediol being between about 6 wt-% in water.

18. The process of claim 16, wherein the extract stream being essentially free of water has a water concentration equal to or less than about 5 vol-%.

19. The process of claim 16, wherein the stationary phase adsorbent is a fluorinated carbon adsorbent.

20. The process of claim 19, wherein the fluorinated carbon adsorbent is a surface modified carbon adsorbent comprising from about 0.5 to about 5 weight percent fluoride.

21. The process of claim 19, wherein the fluorinated carbon adsorbent is a surface modified carbon adsorbent comprising from about 1.5 to about 5 weight percent fluoride.

22. The process of claim 16, wherein the stationary phase adsorbent is a modified C18 silica gel.

23. The process of claim 16, wherein the mobile phase desorbent is methanol.

24. The process of claim 16, wherein the mobile phase desorbent is ethanol.

25. The process of claim 16, wherein the mobile phase desorbent is MTBE.

26. The process of claim 16, wherein the raffinate stream is essentially free of ethanol and 2,3-butanediol.

27. The process of claim 24, wherein the raffinate stream being essentially free of ethanol and 2,3-butanediol, said raffinate stream having a combined concentration of ethanol and butanediol equal to or less than about 5 vol-%.

28. The process of claim 1, wherein the feed stream comprises less than 2 wt-% of 2,3-butanediol.

29. The process of claim 16, wherein the regeneration section comprises a first regeneration section being regenerated with steam having a steam temperature of from about 100° C. to about 120° C. to provide a spent steam stream, condensing the spent steam stream to form a condensate stream at a condensate temperature of from 20° C. to 40° C., and combining the condensate stream with the filtered feed stream prior to passing the filtered feed stream to the SMB zone.

30. The process of claim 16, wherein the SMB zone comprises 10 adsorption beds, the desorption section comprising 2 adsorbent beds, the rectification section comprising 3 adsorbent beds, the adsorption section comprising 3 adsorbent beds, and the regeneration section comprising 2 adsorbent beds.

31. The process of claim 16, further comprising returning a portion of the ethanol stream to the SMB zone as the regeneration stream.

32. The process of claim 16, wherein the mobile phase desorbent comprises ethanol and at least a portion of the ethanol stream of step (f) is stripped to provide a stripped ethanol stream and the stripped ethanol stream is returned to the SMB zone as the mobile phase desorbent.

33. The process of claim 16, wherein the recovery zone of step (f) the extract stream is passed to an ethanol separator to provide the ethanol stream and an ethanol separator bottoms comprising butanediol and acetic acid and soluble biomass, passing the separator bottoms to an acetic acid recovery column to provide an acetic acid stream and a bottoms stream comprising butanediol and soluble biomass, and passing the bottoms stream to a butanediol column to provide the butanediol stream and a soluble biomass stream.

34. The process of claim 32, wherein the feed stream is an effluent stream from a biomass fermentation process and the mobile phase desorbent comprises ethanol wherein the raffinate comprising ethanol and water is passed to an azeotrope separation column to provide an ethanol stream and a waste water stream, passing the ethanol stream to an ethanol dryer to provide a fuel grade ethanol product.

35. The process of claim 1, wherein the biomass effluent stream is derived from the fermentation of corn, sugarcane, molasses, glucose, xylose, arabinose, and gases.

* * * * *